United States Patent [19]

Friese et al.

[11] Patent Number: 4,999,432

[45] Date of Patent: Mar. 12, 1991

[54] FLUORINATION WITH HYDROGEN FLUORIDE

[75] Inventors: David D. Friese, Antioch; Jerry M. Elledge, Martinez, both of Calif.

[73] Assignee: DowElanco, Indianapolis, Ind.

[21] Appl. No.: 399,748

[22] Filed: Aug. 28, 1989

[51] Int. Cl.$^5$ .................. C07D 213/61; C07D 213/84
[52] U.S. Cl. .................................... 546/286; 546/345
[58] Field of Search ............................... 546/286, 345

[56] References Cited

U.S. PATENT DOCUMENTS

| | | | |
|---|---|---|---|
| 4,547,577 | 11/1985 | Gatlin et al. | 546/345 |
| 4,590,279 | 5/1986 | Fung et al. | 546/345 |
| 4,650,875 | 3/1987 | Fujioka | 546/345 |
| 4,680,406 | 6/1987 | Fujioka | 546/345 |
| 4,782,161 | 11/1988 | DesJardin et al. | 546/345 |
| 4,831,148 | 5/1989 | Schurter | 546/345 |

FOREIGN PATENT DOCUMENTS 2006607 9/1970 Fed. Rep. of Germany .
1272475 4/1972 United Kingdom .

Primary Examiner—Joseph Paul Brust
Assistant Examiner—Jacqueline Haley
Attorney, Agent, or Firm—D. Wendell Osborne

[57] ABSTRACT

Fluoropyridine compounds having a fluoro substituent in at least one of the 2-, 4-, and 6-positions are prepared by treatment of an appropriate 2-, 4-, or 6-chloropyridine compound with excess hydrogen fluoride in a dipolar, aprotic solvent at an elevated temperature and super-atmospheric pressure. Thus, 3,5-dichloro-2,4,6-trifluoropyridine is prepared by heating a mixture of pentachloropyridine, N-methyl-2-pyrrolidinone, and hydrogen fluoride at about 220° C. and about 900 kiloPascals of pressure.

12 Claims, No Drawings

FLUORINATION WITH HYDROGEN FLUORIDE

BACKGROUND OF THE INVENTION

The present invention relates to a process for preparing fluoropyridines from chloropyridines by treatment with hydrogen fluoride.

Fluoropyridines, such as 3,5-dichloro-2,4,6-trifluoropyridine, are valuable intermediates useful in the preparation of herbicides, insecticides, fungicides, fixed dyes, and other end use products. Certain of these compounds are taught to be preparable from the corresponding chloropyridines by exchange with alkali metal fluorides, either in a melt and in certain dipolar, aprotic solvents. Certain of them are also taught to be preparable from the corresponding chloropyridines by exchange with hydrogen fluoride, either in the vapor phase or neat. None of the methods are entirely satisfactory, however. Methods employing an alkali metal fluoride produce an alkali metal chloride as a by-product which must be disposed of, sold, or recycled. Known methods employing hydrogen fluoride (see, for example, British Patent Application No. 1,272,475, published Apr. 26, 1972) are slow, require metal halide or carbon catalysts, and produce only low yields of the desired fluoropyridines.

SUMMARY OF THE INVENTION

It has now been found that fluoropyridine compounds can be prepared in good yield and at a reasonable reaction rate by combining chloropyridine compounds and hydrogen fluoride in a dipolar, aprotic solvent at an elevated temperature and an elevated pressure.

The invention includes a process which comprises preparing a fluoropyridine compound of the general formula

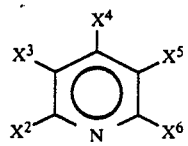

wherein
$X^2$, $X^3$, $X^4$, $X^5$, and $X^6$ each independently represent F, Cl, $CF_3$, $CHF_2$, CN, H, or $CH_3$ with the provisos that at least one of $X^2$, $X^4$, and $X^6$ represents F and no more than two of $X^2$, $X^3$, $X^4$, $X^5$, and $X^6$ represent H or $CH_3$
by heating a mixture of a chloropyridine compound of the same general formula wherein
$X^2$, $X^3$, $X^4$, $X^5$, and $X^6$ each independently represent F, Cl, $CF_3$, $CHF_2$, CN, H, or $CH_3$ with the provisos that at least one of $X^2$, $X^4$, and $X^6$ represents Cl and no more than two of $X^2$, $X^3$, $X^4$, $X^5$, and $X^6$ represent H or $CH_3$,
hydrogen fluoride, and a dipolar, aprotic solvent to a temperature of between about 160° C. and about 300° C. and a pressure of between about 100 kiloPascals and about 7,000 kiloPascals for a sufficient amount of time to exchange at least one chlorine substituent in a 2-, 4-, or 6-position with fluorine.

Preferred chloropyridine starting materials include pentachloropyridine, 2,3,5,6-tetrachloropyridine, and 2,6-dichloro-4-(trifluoromethyl)pyridine. Preferred dipolar, aprotic solvents include N-methyl-2-pyrrolidinone.

The fluoropyridine products obtained, such as 3,5-dichloro-2,4,6-trifluoropyridine, 3,5-dichloro-2,6-difluoropyridine, and 2,6-difluoro-4-(trifluoromethyl)-pyridine, which are useful as chemical intermediates for the preparation of a variety of valuable compounds, are produced in the process in good yield and in a reasonable amount of time without the generation of an alkali metal chloride by-product. The process, additionally obviates the need for catalysts, such as metal halides and activated carbon, that are often employed in hydrogen fluoride exchange reactions.

DETAILED DESCRIPTION OF THE INVENTION

The process of the present invention is applicable to the preparation of a range of fluoropyridine compounds of the general formula

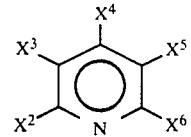

wherein $X^2$, $X^3$, $X^4$, $X^5$, and $X^6$ each independently represent F, Cl, $CF_3$, $CHF_2$, CN, H, or $CH_3$ with the provisos that at least one of $X^2$, $X^4$, and $X^6$ represents F and no more than two of $X^2$, $X^3$, $X^4$, $X^5$, and $X^6$ represent H or $CH_3$. Such compounds can be characterized as pyridines possessing at least one fluoro substituent in a 2-, 4-, or 6-position and possessing at least three total electron withdrawing substituents selected from F, Cl, $CF_3$, $CHF_2$, and CN. Examples of fluoropyridine products preparable by the process include 3,5-dichloro-2,4,6-trifluoropyridine, 2,4-difluoro-3,5,6-trichloropyridine, 2,6-difluoro-3,4,5-trichloropyridine, 3,5-dichloro-2,6-difluoropyridine, 2,6-difluoro-4-(trifluoromethyl)pyridine, 2,6-difluoro-5-cyanopyridine, 4-methyl-2,3,5-trifluoropyridine, 2,4-difluoro-6-(difluoromethyl)pyridine, 3,5-dichloro-2,6-difluoro-4-(trifluoromethyl)pyridine, and 3,5-dichloro-4,6-difluoro-2-cyanopyridine. A preferred product of the process is 3,5-dichloro-2,4,6-trifluoropyridine.

The starting material chloropyridine compounds to which the process is applicable have the general formula

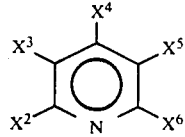

wherein $X^2$, $X^3$, $X^4$, $X^5$, and $X^6$ each independently represent F, Cl, $CF_3$, $CHF_2$, CN, H, or $CH_3$ with the provisos that at least one of $X^2$, $X^4$, and $X^6$ represents Cl and no more than two of $X^2$, $X^3$, $X^4$, $X^5$, and $X^6$ represent H or $CH_3$. Such compounds can be characterized as pyridines possessing at least one chloro substituent in a 2-, 4-, or 6-position and possessing at least three total electron withdrawing substituents selected from F, Cl, $CF_3$, $CHF_2$, and CN. Examples of chloropyridine starting materials include pentachloropyridine, 2,6-difluoro-3,4,5-trichloropyridine, 2,3,5,6-tetrachloropyridine, 2,3,4,5-tetrachloropyridine, 2,3,4,6-tetrachloropyridine, 2,3,5-trichloropyridine, 2,6-dichloro-4-cyanopyridine, 2,3,4-trichloro-6-methylpyridine, 2,4-dichloro-6-(difluoromethyl)pyridine, 2,3,6-trichloro-5-(trifluoromethyl)pyridine, 2,6-dichloro-4-(trifluoromethyl)pyridine, and 2-cyano-4,6-dichloro-3,5-difluoropyridine.

The process of the present invention requires a dipolar, aprotic solvent. This class of solvents is well known in the art and includes solvents such as N,N-dimethylformamide, N,N-dimethylacetamide, N-methyl-2-pyrrolidinone, 1,3-dimethyl-2-imidazolidinone, sulfolane, dimethyl sulfoxide, and hexamethylphosphoramide. N-methyl-2-pyrrolidinone is a preferred solvent. A sufficient amount of solvent is generally employed to dissolve the starting chloropyridine compound at higher temperatures. Generally, a ratio of solvent to chloropyridine compound of about 1:1 to about 20:1 is suitable.

The hydrogen fluoride is generally employed in excess. Typically, about 2 to about 50 moles of hydrogen fluoride are employed for every chloro substituent exchanged. Thus, for example, to prepare 3,5-dichloro-2,4,6-trifluoropyridine from pentachloropyridine about 6 to about 150 moles of hydrogen fluoride are generally employed for every mole of pentachloropyridine. About 3 to about 40 moles are generally preferred.

The process is conducted by heating a mixture of the starting chloropyridine, a dipolar, aprotic solvent, and hydrogen fluoride at a sufficiently high temperature, under a sufficiently high pressure, and for a sufficient amount of time to exchange at least one chloro substituent in the 2-, 4-, or 6-position to a fluoro substituent in substantial conversion. Temperatures of about 160° C. to about 300° C. are usually suitable and temperatures of about 200° C. to about 250° C. are generally preferred. Pressures of about 100 to about 7,000 kiloPascals are usually suitable and pressures of about 300 to about 3,600 kiloPascals are generally preferred. Pressures above those naturally attained in the system are generally achieved by adding an inert gas, such as nitrogen or argon.

When a substantial amount of the desired fluoropyridine compound has formed it can be recovered by conventional means. Methods involving distillation are often preferred. Since each of the reactants and products is volatile, separations are readily made by distillation. It is also appropriate to dilute with water and separate the fluoropyridine as an insoluble liquid or solid.

It is possible, and in some instances preferable, to conduct the process in such a manner that the hydrogen chloride formed as a by-product distills from the reaction mixture as it forms. A reactor equipped with a fractionating distillation column capable of operating under pressure is required. When this embodiment of the invention is employed, it is possible to use less of an excess of hydrogen fluoride than when the hydrogen chloride is left in the mixture. Thus, it is preferred to employ about 5 to about 40 moles of hydrogen fluoride for every chloro substituent exchanged if the hydrogen chloride is not removed but only about 3 to about 10 if it is.

It is further possible, and in some instances preferable, to conduct the process in such a manner that the product fluoropyridine as well as the by-product hydrogen chloride is removed from the reaction mixture as it forms. In this embodiment of the process a more volatile portion of the reaction mixture is continuously removed from the mixture by distillation. The distillate obtained is fractionally distilled to separate and recover the desired fluoropyridine product and separate the hydrogen chloride by-product from the hydrogen fluoride reactants, any chloropyridine reactant or intermediate, and any solvent present in the distillate. The reactants, intermediates, and solvents are continuously returned to the reactor for further processing.

The process can be conducted in either a batch mode or a continuous mode.

The process can be carried out in any reactor that is compatible with the reactants and products and is capable of super-atmospheric pressure operation. Materials of construction resistant to corrosion by hydrogen chloride and hydrogen fluoride, are generally employed. Reactors coated with a fluorinated polymer, such as polytetrafluoroethylene, are especially useful for the process. When a metal that is too susceptible to corrosion by hydrogen chloride or hydrogen fluoride is employed, reductive dechlorination is a significant side reaction.

The following example is presented to illustrate the process of the invention. It should not be construed as limiting.

EXAMPLE

Example 1

Preparation of 3,5-Dichloro-2,4,6-trifluoropyridine and 2,6-Difluoro-3,4,5-trichloropyridine From Pentachloropyridine A 250 milliliter polytetrafluoroethylene lined reactor equipped with stirring and heating means was employed. Pentachloropyridine (15.5 grams, 0.0616 mole), hydrogen fluoride (98.2 grams, 4.91 moles) and N-methyl-2-pyrrolidinone (124 grams) were placed in the reactor and heated with stirring at about 220° C. Nitrogen gas was introduced to increase the pressure to about 900 kiloPascals. The reactor contents were sampled at intervals and the samples were analyzed by gas-liquid chromatography. The results are given in the following table

| Run Time, Hours | Pentachloropyridine, Percent | Monofluorotetrachloropyridines, Percent | Difluorotrichloropyridines,* Percent | 3,5-Dichloro-2,4,6-trifluoropyridine, Percent |
|---|---|---|---|---|
| 0.0 | 99.6 | 0.0 | 0.0 | 0.0 |
| 0.5 | 43.8 | 42.1 | 2.6 | 0.8 |
| 4.5 | 3.9 | 48.5 | 38.6 | 5.4 |
| 7.5 | 2.0 | 35.8 | 47.3 | 9.0 |
| 13.5 | 0.7 | 20.5 | 58.7 | 15.5 |
| 26.0 | 0.0 | 7.3 | 42.2 | 36.4 |
| 30.5 | 0.0 | 6.1 | 46.2 | 42.8 |

*A mixture of isomers in which 2,6-difluoro-3,4,5-trichloropyridine is predominant.

What is claimed is:

1. A process which comprises preparing a fluoropyridine compound of the general formula

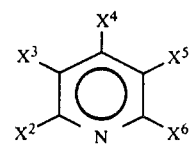

wherein

X$^2$, X$^3$, X$^4$, X$^5$, and X$^6$ each independently represent F, Cl, CF$_3$, CHF$_2$, CN, H, or CH$_3$ with the provisos that at least one of X$^2$, X$^4$, and X$^6$ represents F and no more than two of X$^2$, X$^3$, X$^4$, X$^5$, and X$^6$ represent H or CH$_3$ by heating a mixture of a chloropyridine compound of the same general formula wherein X$^2$, X$^3$, X$^4$, X$^5$, and X$^6$ each independently represent F, Cl, CF$_3$, CHF$_2$, CN, H, or CH$_3$ with the provisos that at least one of X$^2$, X$^4$, and X$^6$ represents Cl and no more than two of X$^2$, X$^3$, X$^4$, X$^5$, and X$^6$ represent H or CH$_3$, hydrogen fluoride, and a dipolar, aprotic solvent to a temperature of between about 160° C. and about 300° C. and a pressure of between about 100 and about 7,000 kiloPascals for a sufficient amount of time to exchange at least one chlorine substituent in a 2-, 4-, or 6-position with fluorine, and, optionally recovering the fluoropyridine compound.

2. A process according to claim 1 wherein the chloropyridine compound is pentachloropyridine.

3. A process according to claim 1 wherein the chloropyridine compound is 2,3,5,6-tetrachloropyridine.

4. A process according to claim 1 wherein the fluoropyridine compound is 3,5-dichloro-2,4,6-trifluoropyridine, 2,6-difluoro-3,4,5-trichloropyridine, or 3,5-dichloro-2,6-difluoropyridine.

5. A process according to claim 4 wherein the fluoropyridine compound is 3,5-dichloro-2,4,6-trifluoropyridine.

6. A process according to claim 5 wherein the chloropyridine compound is pentachloropyridine and the fluoropyridine compound is 3,5-dichloro-2,4,6-trifluoropyridine.

7. A process according to claim 1 wherein the temperature is about 200° C. to about 250° C.

8. A process according to claim 1 wherein the pressure is about 300 to about 3,600 kiloPascals.

9. A process according to claim 1 wherein the solvent is N-methyl-2-pyrrolidinone.

10. A process according to claim 1 wherein the hydrogen chloride by-product is removed as it forms by distillation.

11. A process according to claim 1 wherein the fluoropyridine compound is recovered.

12. A process according to claim 11 wherein the fluoropyridine compound is recovered continuously by distillation.

* * * * *